(12) United States Patent
Ricke et al.

(10) Patent No.: US 10,232,063 B2
(45) Date of Patent: Mar. 19, 2019

(54) METHOD FOR TREATING LUNG CARCINOMA

(71) Applicant: Sirtex Medical Limited, North Sydney, New South Wales (AU)

(72) Inventors: Jens Ricke, Potsdam (DE); Holger Amthauer, Magdeburg (DE); Oliver Grober, Magdeburg (DE)

(73) Assignee: Sirtex Medical Limited, North Sydney, New South Wales (AU)

( * ) Notice: Subject to any disclaimer, the term of this patent is extended or adjusted under 35 U.S.C. 154(b) by 313 days.

(21) Appl. No.: 14/793,603

(22) Filed: Jul. 7, 2015

(65) Prior Publication Data

US 2016/0008497 A1   Jan. 14, 2016

Related U.S. Application Data

(60) Provisional application No. 62/022,645, filed on Jul. 9, 2014.

(51) Int. Cl.
*A61K 51/12* (2006.01)
*A61K 45/06* (2006.01)
*A61N 5/10* (2006.01)

(52) U.S. Cl.
CPC .......... *A61K 51/1251* (2013.01); *A61K 45/06* (2013.01); *A61N 5/1001* (2013.01); *A61N 2005/1021* (2013.01)

(58) Field of Classification Search
CPC ................ A61K 45/06; A61K 51/1251; A61N 2005/1021; A61N 5/1001
See application file for complete search history.

(56) References Cited

U.S. PATENT DOCUMENTS

2005/0220705 A1* 10/2005 Brooks ................ A61K 31/136
424/1.49

OTHER PUBLICATIONS

Ricke, et al.; Y90-Radioembolization of Lung Metastases via the Bronchial Artery: A Report of 2 Cases; Cardiovasc Intervent Radio!, Jul. 10, 2013; pp. 1-6.

* cited by examiner

*Primary Examiner* — Christine H Matthews
(74) *Attorney, Agent, or Firm* — Stites & Harbison PLLC; Richard S. Myers, Jr.

(57) ABSTRACT

Accordingly, the present invention provides a method of treating lung neoplasia in a subject in need of treatment, by subjecting the patient to SIRT.

7 Claims, 4 Drawing Sheets

METHOD FOR TREATING LUNG CARCINOMA

TECHNICAL FIELD

This invention relates to a method for treating Lung Cell Carcinomas (LCC) using Selective Internal Radiation Therapy (SIRT).

BACKGROUND ART

In patients with diffuse lung metastases and no systemic chemotherapy option, therapeutic alternatives are scarce.

Locoregional transcatheter treatment of lung tumors found considerable interest in the 1950s and 1960s, with a number of groups delivering intra-arterial chemotherapy via the bronchial arteries. Japanese groups replicated these approaches in the 1990s in an attempt to downstage locally unresectable stage III bronchial carcinoma. Results of small single-arm cohorts were published, but a transition of these activities to phase III is still missing.

Metastatic disease of the lung is a frequent finding in solid tumors. Aggressive treatment of lung tumors by resection or ablation has been established in various entities, such as colorectal cancer, melanoma, renal cancer, sarcoma, non-small cell lung cancer (NSCLC) and others. However, in multiple lesions surgical resection is limited by the residual lung capacity.

Local ablation such as by radiofrequency ablation (RFA) is well established in solitary lesions but rarely applicable if the lesion number is greater than three or the lesion diameter is larger than 3 cm. Stereotactic irradiation or CT-guided brachytherapy have demonstrated favourable results but, as is RFA, are limited to small lesion numbers and cannot be applied in diffuse lung metastases.

Some authors have described the treatment of lung malignancies by chemoembolization (TPCE) via the pulmonary artery. However, despite reports of moderate response rates the approach remains controversial. Image data suggest that metastases might not be supplied by pulmonary arteries but rather by the bronchial artery, and lipiodol from TPCE may even be visualized in the pulmonary parenchyma only, sparing the targeted metastases. Arterial chemoperfusion via the bronchial artery has raised strong interest in the 1960s in attempts to improve the cytotoxic therapy of lung malignancies.

Jonas at al. [Jonas A M, Carrington C B (1969) Vascular patterns in primary and secondary pulmonary tumors in the dog. *Am J Pathol* 56(1):79-95] published data for in vivo and postmortem injection of contrast dye, gelatin, or vinylite-corrosion cast in dogs with both primary and secondary lung malignancies. All casts and the in vivo injections revealed proliferated or increased calibers of bronchial arteries supplying 100% of the primary or secondary malignancies identified. Bronchial to pulmonary artery anastomoses were not found. These results have been reproduced in a number of case reports or small cohorts in humans. It should nevertheless be noted that even though each lung malignancy displayed a bronchial artery to supply its gross mass, the tumor margin in some instances displayed a growth pattern, such as "cancerous pneumonia," into alveolar lumen with septa still intact. In this situation, a pulmonary artery supply to the tumor margin was demonstrated. In support of these results, a recent perfusion study has demonstrated a dual perfusion pattern of primary lung cancer in 13 patients with the central bronchial perfusion being dominant with moderate dependency on tumor size, i.e., the larger the tumor, the stronger the dominance of the bronchial artery for tumor perfusion.

Despite the many refinements in surgical techniques, the increase in knowledge around the blood supply to carcinomas in the lung and new targeted pharmacologic agents, lung tumors remain one of the most lethal cancers. Adjuvant treatment options are limited and there is a clear need for further research and new treatment approaches in this field.

Selective internal radiation therapy (SIRT), which is the intra-arterial delivery of radioactive microparticles to tumours, has an established therapeutic role in the management of inoperable primary and metastatic liver tumours. However, the utility of SIRT for the management of LCC remains largely unexplored and unknown in light of whether the same endovascular principles may be deployed and more relevantly what dose is required in cases of lung trauma and in the management of a range of benign and malignant conditions.

It is against this background that the present invention has been developed.

SUMMARY OF INVENTION

The inventor has revealed that the method of the invention can provide an effective treatment in cases of lung trauma and in the management of a range of benign and malignant lung conditions.

According to the method of the present invention there is provided a treatment for lung neoplastic conditions in a subject comprising subjecting the subject to SIRT, wherein (i) the prescribed activity of the irradiated microparticles used in the selective internal radiation therapy is 150 to 300 MBq and (ii) the therapy delivers a tumor dose of up to 6 MBq/ml of tumor volume to the site of treatment in the lung. Preferably the site of treatment is restricted to the neoplasia.

BRIEF DESCRIPTION OF THE DRAWINGS

Other aspects and advantages of the invention will become apparent to those skilled in the art from a review of the ensuing description of several non-limiting embodiments thereof.

DETAILED DESCRIPTION OF THE INVENTION

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The invention described herein may include one or more range of values (for example, size, displacement and field strength etc.). A range of values will be understood to include all values within the range, including the values defining the range, and values adjacent to the range that lead to the same or substantially the same outcome as the values immediately adjacent to that value which defines the boundary to the range. For example, a person skilled in the field will understand that a 10% variation in upper or lower limits of a range can be totally appropriate and is encompassed by the invention. More particularly, the variation in upper or lower limits of a range will be 5% or as is commonly recognised in the art, whichever is greater.

Throughout this specification relative language such as the words 'about' and 'approximately' are used This language seeks to incorporate 10% variability to the specified number or range. That variability may be plus 0% or negative 10% of the particular number specified The present invention is not to be limited in scope by the following specific embodiments. This description is intended for the purpose of exemplification only. Functionally equivalent products, compositions and methods are within the scope of the invention as described herein.

Features of the invention will now be discussed with reference to the following non-limiting description and examples.

The present invention provides a method of treating lung neoplasia in a subject in need of treatment, by subjecting the patient to SIRT.

In the method of the present invention, a lung neoplasia is treated in a subject in need of treatment comprising the step of: administering to the lung neoplasia an amount of microparticles that delivers radiation at a tumor dose of up to 6 MBq/ml of tumor volume to the site of treatment in the lung.

In a preferred form of the invention the microparticles are suitable for SIRT. Ideally the microparticles will carry a level of radioactivity that is between about 150 to 300 MBq. In a form, the activity of the microparticles is between about 180 and 250 MBq. Most preferably the radioactivity is about 200 MBq. Ideally, it is capped at a maximum of 200 MBq.

In an embodiment of the invention, the radioactivity of the microparticles used in the SIRT is calculated by determining the tumour volume and then adjusting the amount of the radioactive microparticles, having regard to tumour volume, to deliver to the lung neoplasia a radiation dose of up to 6 MBq/ml of tumor volume to the site of treatment in the lung.

In a highly preferred form of the invention the microparticles provide 200 MBq (+/−10%). The microparticles are preferably suspended in sterile water for injection. Each vial of microspheres is in a volume of 5 ml (microparticles and water together). This allows the required activity of the radionucleotide to be manipulated as a volume.

Prefereably the microparticles are labelled with radioactive yttrium-90.

The present invention provides a method of treating neoplasia in a subject in need of treatment. As used herein, "neoplasia" refers to the uncontrolled and progressive multiplication of cells under conditions that would not elicit, or would cause cessation of, multiplication of normal cells. Neoplasia results in the formation of a "neoplasm", which is defined herein to mean any new and abnormal growth, particularly a new growth of tissue, in which the growth is uncontrolled and progressive. Malignant neoplasms are distinguished from benign in that the former show a greater degree of anaplasia, or loss of differentiation and orientation of cells, and have the properties of invasion and metastasis. Thus, neoplasia includes "cancer", which herein refers to a proliferation of cells having the unique trait of loss of normal controls, resulting in unregulated growth, lack of differentiation, local tissue invasion, and metastasis. Neoplasias for which the present invention will be particularly useful include, without limitation, lung cell carcinomas.

As used herein "treatment" includes:
(i) preventing a disease, disorder or condition from occurring in an subject which may be predisposed to the disease, disorder and/or condition but has not yet been diagnosed as having it;
(ii) inhibiting the disease, disorder or condition, i.e., arresting its development; or
(iii) relieving the disease, disorder or condition, i.e., causing regression of the disease, disorder and/or condition.

According to the method of the invention the subject is preferably a mammal (e.g., human beings, domestic animals, and commercial animals, including cows, dogs, monkeys, mice, pigs, and rats), and is most preferably a human.

SIRT

Radiotherapy usually relies on treatment through external beam technologies or more recently through locally administering radioactive materials to patients with cancer as a form of therapy. In some of these, the radioactive materials have been incorporated into small particles, seeds, wires and similar related configurations that can be directly implanted into the cancer. When radioactive particles are administered into the blood supply of the target organ, the technique has become known as Selective Internal Radiation Therapy (SIRT). Generally, the main form of application of SIRT has been its use to treat cancers in the liver.

There are many potential advantages of SIRT over conventional, external beam radiotherapy. Firstly, the radiation is delivered preferentially to the cancer within the target organ. Secondly, the radiation is slowly and continually delivered as the radionuclide decays. Thirdly, by manipulating the arterial blood supply with vasoactive substances, it is possible to enhance the percentage of radioactive particles that go to the cancerous part of the organ, as opposed to the healthy normal tissues. This has the effect of preferentially increasing the radiation dose to the cancer while maintaining the radiation dose to the normal tissues at a lower level.

The technique of SIRT has been previously reported (see, for example, Chamberlain M, et al (1983) *Brit. J. Surg.*, 70: 596-598; Burton M A, et al (1989) *Europ. J. Cancer Clin. Oncol.*, 25, 1487-1491; Fox R A, at al (1991) *Int. J. Rad. Oncol. Biol. Phys.* 21, 463-467; Ho S at al (1996) *Erop J Nuclear Med.* 23, 947-952; Yorke E, at al (1999) *Clinical Cancer Res,* 5 (Suppl), 3024-3030; Gray B N, at al. (1990) *Int. J. Rad. Oncol. Biol. Phys,* 18, 619-623). Treatment with SIRT has been shown to result in high response rates for patients with neoplastic growth in particular with colorectal liver metastases (Gray B. N. et al (1989) *Surg. Oncol,* 42, 192-196; Gray B, et al. (1992) *Aust NZ J Surgery,* 62, 105-110; Gray B N at al. (2000) *GI Cancer,* 3(4), 249-257; Stubbs R, at al (1998) *Hepato-gastroenterology* Suppl II, LXXVII). Other studies have shown that SIRT therapy can also be effective in causing regression and prolonged survival for patients with primary hepatocellular cancer (Lau W, et al (1994) *Brit J Cancer* 70, 994-999; Lau W, at al. (1998) *Int J Rad Oncol Biol Phys.* 40, 583-592). Although SIRT is effective in controlling the liver disease, it is not thought to have an extra-hepatic effect.

SIRT, which may also be known as radio-embolization or microparticle brachytherapy involves two procedural components:

Embolization: injection into the arterial tumour feeding vessels of permanently embolic microparticles which act as the delivery vehicle for the therapeutic moiety, and Irradiation: embolization of microparticles in the distal microvasculature of the tumour delivers high dose irradiation to the tumour microvascular plexus and to tumour cells themselves.

Relevantly, direct irradiation of tissue and microvascular bed destruction, rather than pure embolization is responsible for the tissue destructive effects of SIRT therapy.

Broadly speaking radioactive microparticles do not exhibit pharmacodynamics in the classic sense, but induce cell damage by emitting radiation. Once implanted, radioactive microparticles remain within the vasculature of tumours. They are not phagocytised nor do they dissolve or degrade after implantation. High radiation emitted from the radioactive microparticles is preferably cytocidal to cells within the range of the radiation. After the radioactive microparticle has decayed, the non-radioactive microparticles remain intact and are not removed from the body.

Intrinsic to the concept of SIRT is the preferential placement of the radioactive microparticles selectively into the distal microvascular supply of tumours. This may be achieved by direct injection of the microparticles or through the manipulation of blood flow into and out of the target organ.

Accordingly administration of radionuclide microparticles may be by any suitable means, but preferably by delivery to the relevant artery. For example in treating LCC, administration is preferably by laparotomy to expose the bronchial artery.

Pre or co-administration of another agent may prepare the tumour for receipt of the particulate material, for example a vasoactive substance, such as angiotension-2 to redirect arterial blood flow into the tumour. Delivery of the particulate matter may be by single or multiple doses, until the desired level of radiation is reached.

Microparticles

The term microparticle is used in this specification as an example of a particulate material, it is not intended to limit the invention to microparticles, as the person skilled in the art will appreciate that the shape of the particulate material while preferably without sharp edges or points that could damage the patients arteries or catch in unintended locations, is not limited to spheres. Nor should the term microparticle be limited to spheres. Preferably the particulate material is substantially spherical, but need not be regular or symmetrical in shape.

The microparticles also need not be limited to any particular form or type of microparticle. Any microparticles may be used in the present invention provided the particles are capable of receiving a radionuclide such as through impregnation, absorbing, coating or more generally bonding the particles together.

In one particular form of the invention the microparticles are prepared as polymeric particles. In another form of the invention the microparticles are prepared as ceramic particles (including glass).

Where the microparticles are prepared as a polymeric matrix there are a range of methods that may be used to prepare such particles. By way of example a description of such particles including methods for their production and formulation as well as their use is provided in co-owned European application number 20010978014, of which the teachings therein are expressly incorporated herein by reference.

Where the microparticles are ceramic particles (including glass) the selected particles will usually possess the following properties:

the particles will generally be biocompatible, such as calcium phosphate-based biomedical ceramics or glass.

the particles will generally comprise a radionuclide that preferably has sufficiently high energy and an appropriate penetration distance, which are capable of releasing their entire energy complement within the tumour tissue to effectively kill the cancer cells and to minimize damage to adjacent normal cells or to attending medical personnel. The level of radiation activity of the ceramic or glass will be selected and fixed based upon the need for therapy given the particular cancer involved and its level of advancement. The ideal half-life of the radionuclides is somewhere between days and months. On the one hand, it is impractical to treat tumours with radionuclides having too short a half-life, this characteristic limiting therapy efficiency. On the other hand, in radiotherapy it is generally difficult to trace and control radionuclides having a long half-life.

the particles must be of a suitable size. The size of the particles for treatment depends upon such variables as the surface area of the tumour, capillary permeability, and the selected method of introduction into the tumour i.v. versus implant by surgical operation).

some ceramic processes involve inclusion of extraneous substances as contaminants that might produce undesired radionuclides. Should these be well taken care of, the size of the particles can then be controlled by granulation and meshing.

There are many processes for producing small granular ceramic or glass particles. One of these involves the introduction of small amounts of the ceramic particles passing through a high-temperature melting region. Ceramic spherules are yielded by surface tension during melting. After the solidification, condensation, collection and sorting processes, ceramic spherules of various sizes can be obtained. The particle size of ceramic spheroid can be controlled by the mass of granules introduced into the high-temperature melting region or can be controlled by collecting spheroids of various sizes through the selection of sedimentary time during liquid-sedimentation.

The ceramic or glass materials for preparing those particles can be obtained commercially or from ultra-pure ceramic raw materials if the commercial products do not meet specifications for one reason or another. The ceramic or glass particles for radiation exposure in this invention can be yielded by traditional ceramic processes, which are well known by those skilled in this art. The ceramic processes such as solid-state reaction, chemical co-precipitation, sol-gel, hydrothermal synthesis, glass melting, granulation, and spray pyrolysis can be applied in this invention for the production of specific particles.

The ceramic or glass particles of suitable size which are obtained commercially or which are produced by the processes described above are washed twice with distilled water. Then the supernatant is decanted after sedimentation for 3 minutes. The above two steps are repeated 3 times to remove the micro-granules adhering on the surfaces of the particles. Then a certain amount of ceramic or glass particles prepared from the processes described above are introduced into a quartz tube. After being sealed, the quartz tube is placed inside a plastic irradiation tube, then the irradiation tube is closed. The irradiation tube is put into a vertical tube of the nuclear reactor and the multiple tube assembly is irradiated with an approximated neutron flux for an approximated exposed period (e.g., for about 24 to about 30 hours). Following exposure, the irradiation tube is taken out of the nuclear reactor for cooling. According to this method, ceramic or glass particles carrying radionuclides can be generated.

The microparticles of the invention, be they polymer or ceramic based, can be separated by filtration or other means known in the art to obtain a population of microparticles of a particular size range that is preferred for a particular use. The size and shape of the microparticles is a factor in the distribution and drug delivery in the tissues.

When microparticles or other small particles are administered into the arterial blood supply of a target organ, it is desirable to have them of a size, shape and density that results in the optimal homogeneous distribution within the target organ. If the microparticles or small particles do not distribute evenly, and as a function of the absolute arterial blood flow, then they may accumulate in excessive numbers in some areas and cause focal areas of excessive radiation.

The ideal particle for injection into the blood stream has a very narrow size range with an SD of less than 5%, so as to assist in even distribution of the microparticles within the target organ, particularly within the lung and would be sized in the range 5-200 micron, preferably 15-100 micron, and preferably 20-60 micron, and most preferably 20-35 micron.

If the particles are too dense or heavy, then they will not distribute evenly in the target organ and will accumulate in excessive concentrations in areas that do not contain the neoplastic growth. It has been shown that solid, heavy microparticles distribute poorly within the parenchyma of the liver when injected into the artenal supply of the liver. This, in turn, decreases the effective radiation reaching the neoplastic growth in the target organ, which decreases the ability of the radioactive microparticles to kill the tumour cells. In contrast, lighter microparticles with a specific gravity of the order of less than 2.0 distribute well within the liver. When used in the lung The particulate material is preferably low density, more particularly a density below 3.0 g/cc, even more preferably below 2.8 g/cc, 2.5 g/cc, 2.3 g/cc, 2.2 g/cc or 2.0 g/cc.

Radioactive Particulate Material

For radioactive particulate material to be used successfully for the treatment of neoplastic growth, the radiation emitted should be of high energy and short range. This ensures that the energy emitted will be deposited into the tissues immediately around the particulate material and not into tissues that are not the target of the radiation treatment. In this treatment mode, it is desirable to have high energy but short penetration beta-radiation, which will confine the radiation effects to the immediate vicinity of the particulate material. There are many radionuclides that can be incorporated into microparticles that can be used for SIRT. Of particular suitability for use in this form of treatment is the unstable isotope of yttrium (Y-90). Yttrium-90 is a high-energy pure beta-emitting isotope with no primary gamma emission. The maximum energy of the beta particles is 2.27 MeV, with a mean of 0.93 MeV. The maximum range of emissions in tissue is 11 mm, with a mean of 2.5 mm. The half-life of yttrium-90 is 64.1 hours. In use requiring the isotope to decay to infinity, 94% of the radiation is delivered in 11 days leaving only background radiation with no therapeutic value. The microparticles themselves are a permanent implant and each device is for single patient use.

The radionuclide which is incorporated into the microparticle in accordance with the present invention is preferably yttrium-90, but may also be any other suitable radionuclide which can be precipitated in solution, of which the isotopes of lutetium, holmium, samarium, iodine, phosphorous, iridium and rhenium are some examples.

Preferably the radionuclide is stably incorporated into the particulate material or polymeric matrix such that the incorporated radionuclide does not substantially leach out of the particulate material under physiological conditions such as in the patient or in storage. The leaching of radionuclides from the particular material can cause non-specific radiation of the patient and damage surrounding tissue. Preferably the amount of leaching is less than 5%, more preferably less than 4%, 3%, 2%, 1% or 0.9%, 0.8%, 0.7%, 0.6%, 0.5%, 0.4%, 0.3%, 0.2% or 0.1%. One method of assessing leaching is by adjusting a sample to pH 7.0 and agitating in a water bath at 37° C. for 20 minutes. A 100 µL sample is counted for beta emission in a Geiger-Müller counter. Another representative 100 µL sample is filtered through a 0.22 µm filter and the filtrate counted for beta emission in the Geiger-Müller counter. The percent unbound radionuclide is calculated by $$\frac{FiltrateCount}{SampleCount} \times 100 = \% \ UnboundRadionuclide$$

Desirably, the radionuclide is stably incorporated into the microparticle.

In a preferred form of the invention the microparticle is prepared as a particulate material comprising a polymeric matrix, which is an ion exchange resin, particularly a cation exchange resin. Preferably the ion exchange resin comprises a partially cross linked aliphatic polymer, including polystyrene. One particularly preferred cation exchange resin is the styrene/divinylbenzene copolymer resin commercially available under the trade name Aminex 50W-X4 (Biorad, Hercules, Calif.). However, there are many other commercially available cation exchange resins that are suitable, including styrene/divinylbenzene copolymer resin with varying degrees of cross-linking.

It is also desirable to have the particulate material manufactured so that the suspending solution has a pH less than 9. If the pH is greater than 9 then this may result in irritation of the blood vessels when the suspension is injected into the artery or target organ. Preferably the pH is less than 8.5 or 8.0 and more preferably less than 7.5.

According to the invention the person skilled in the art will appreciate that SIRT may be applied by any of a range of different methods, some of which are described in U.S. Pat. Nos. 4,789,501, 5,011,677, 5,302,369, 6,296,831, 6,379,648, or WO applications 200045826, 200234298 or 200234300.

In one embodiment, the method of the present invention is carried out by firstly irradiating yttria (yttrium oxide) in a neutron beam to activate yttria to the isotope yttrium-90, The yttrium-90 oxide is then solubilised, for example as yttrium-90 sulphate solution. The ion exchange resin is preferably provided in the form of an aqueous slurry of microparticles of ion exchange resin having a particle size 30 to 35 microns, and the yttrium-90 sulphate solution is added to the slurry to absorb the yttrium-90 into the ion exchange resin microparticles. Subsequently, the yttrium-90 is precipitated, for example by addition of tri-sodium phosphate solution, to stably incorporate the yttrium-90 into the microparticles. The particulate material may be combined with a solution of the radionuclide or the salt of the radionuclide may be combined with the particulate matter, in a solution suitable for solubilising the radionuclide.

Alternate sources of yttrium-90 may be used in the production of these microparticles. For example, a highly pure source of yttrium-90 may be obtained by extracting yttrium-90 from a parent nuclide and using this extracted yttrium-90 as the source of the soluble yttrium salt that is then incorporated into the polymeric matrix of the microparticles. For example, the method of the present invention is carried out by sourcing yttrium-90 from a generator, such as a $^{90}SR/^{90}Y$ generator In order to decrease the pH of the suspension containing the microparticles for injection into patients the microparticles may be washed to remove any un-precipitated or loosely adherent radionuclide. According to the method of the present invention the microparticles used in the method are prepared as a suspension at the required pH by precipitating the yttrium with a tri-sodium phosphate solution at a concentration containing at least a three-fold excess of phosphate ion, but not exceeding a 30-fold excess of phosphate ion, and then washing the microparticles with de-ionised water. Another approach, which ensures that the pH of the microparticle suspension is in the desired range, is to wash the resin with a phosphate buffer solution of the desired pH.

Radioactivity of the Particulate Material

The amount of microparticles used in the method and which will be required to provide effective treatment of a neoplastic growth will depend substantially on the radionuclide used in the preparation of the microparticles.

By way of example, an amount of yttrium-90 activity that will result in an inferred radiation dose to a LCC will be approximately 150 to 300 MBq.

The inventors have revealed that in the treatment of neoplasia, treatment is most effective when the activity of yttrium-90 microparticles is approximately 150 to 300 MBq and the therapy delivers a tumor radiation dose of up to 6 MBq/ml of tumor volume to the site of treatment in the lung. Preferably, treatment is most effective when the activity of the microparticles is 100, 110, 120, 130, 140, 150, 160, 170, 180, 190, 200, 210, 220, 230, 240, 250, 260, 270, 280, 290 and 300 MBq and the therapy delivers a tumor radiation dose of up to 6 MBq/ml of tumor volume to the site of treatment in the lung. More specifically, the activity of the microparticles is 180, 190, 200, 210, 220, 230, 240 and 250 MBq and the therapy delivers a tumor radiation dose of up to 6 MBq/ml of tumor volume to the site of treatment in the lung.

In accordance with the invention, SIRT delivers a tumor radiation dose of up to 6 MBq/ml of tumor volume to the site of treatment in the lung. Preferably, the intended radiation dose delivered to the neoplasia in the lung is up to 2 to 5 MBq/ml of tumor volume. More preferably, the radiation dose delivered to the neoplasm in the lung is 2, 2.5, 3, 3.5, 4, 4.5 or 5 MBq/ml of tumor volume.

Variation to the activity of the microparticle used in the SIRT and the intended radiation dose to the neoplasia are two of the variable that must be accounted for in delivering a therapy. Relevantly, any variation of the radiation dose delivered to the neoplasia will cause a consequential variation to the activity of the microparticles used in the method and vice versa.

The lung neoplasm volume is preferably determined from a baseline MRI based 3-D volume reconstruction scan of the abdomen and pelvis. Such a reconstruction is carried out by MeVis Distant Services, Bremen, Germany. The tumour volume was first determined from the screening (i.e. baseline) MRI.

Other Cytotoxic Agents

Desirably microparticles have the potential to interact with other cytotoxic agents and are typically administered concomitantly with either systemic or loco-regional chemotherapeutic agents such as oxiplatin, 5-Fluorouricil or Leucovorin. This interaction may be exploited to the benefit of the patient, in that there can be an additive toxicity on tumour cells, which can enhance the tumour cell kill rate. This interaction can also lead to additive toxicity on non-tumorous cells.

In addition to the identified chemotherapeutic agents and radionuclide microparticles the invention may also include an effect treatment of immunomodulators as part of the therapy. Illustrative immunomodulators suitable for use in the invention are alpha interferon, beta interferon, gamma interferon, interleukin-2, interleukin-3, tumour necrosis factor, granulocyte-macrophage colony stimulating factors, and the like.

The present invention further provides a synergistic combination of antineoplastic agents and an amount of radionuclide-doped microparticles suitable for use in SIRT for treatment of a neoplastic growth. Preferably, the combination is prepared for use in treating a patient with LCC metastases.

The invention also relates to pharmaceutical composition comprising an effective antineoplastic agent and an amount of radionuclide microparticles suitable for use in SIRT for treatment of a neoplastic growth. Preferably, the pharmaceutical composition is prepared for use in treating a patient with LCC metastases.

The invention further relates to a kit for killing LCC in a subject. The kit comprises an effective amount of an antineoplastic agent and an amount of radionuclide microparticles as described above suitable for use in SIRT for treatment of LCC growth. The kit may further comprise an instructional material.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLES

Patient 1

A 45-year-old female presented with lung-only metastatic disease from colorectal cancer initially diagnosed in 2009. After right hemicolectomy, she was treated with adjuvant FOLFOX. Following the development of lung metastases in 2010, she received FOLFIRI and cetuximab as well as 5FU/LV and panitumumab. A resection of lung metastases in 2011 was complicated by sepsis and multi-organ failure. She recovered but presented with progressive lung disease in both lobes in 2012. In this salvage situation, the interdisciplinary decision was to offer a locoregional treatment of the part of the lung that was affected most. The remaining lesions in non-target areas should undergo local ablation afterwards, and lung segments not targeted by Y90-radioembolization were intended to serve as reserve capacity in case lung pneumonitis occurred.

Pulmonary function tests (including vital capacity and forced expiratory volume $FEV_1$) revealed values within normal limits. The patient was evaluated for Y90-microsphere treatment by applying 80 MBq Tc99-MAA (Tc99m-LyoMAA, Covidien, Neustadt, Germany) via the left bronchial artery supplying segments 1-3 and the upper proportion of segment 6 (anatomical taxonomies of Jackson, Boyden and Huber [Boyden E A (1955) Segmental anatomy of the lungs. McGraw Hill, New York and Jackson C L, Huber J F (1943) Correlated applied anatomy of the bronchial tree and lungs with a system of nomenclature. Dis Chest 9:319-326]). The anatomical workup of the bronchial arterial system was identical to a search in patients with suspected bronchial artery bleeding. For identification of the bronchial arterial anatomy, we used standard 5F guiding catheters (5F Imager II, Boston Scientific, Natick, Mass., or 5F Soft-VU Sos Omni, Angiodynamics, Queensbury, USA). For selective catheterisation of the bronchial arteries, we employed a hydrophilic 0.018-inch microcatheter (Micro-Ferret, Cook. Medical, Bloomington, Ind.). SPECT-CT showed strong uptake of Tc99 in the lung nodules of these segments ranging from 4-mm to 5-cm maximum diameter.

Figure 1:
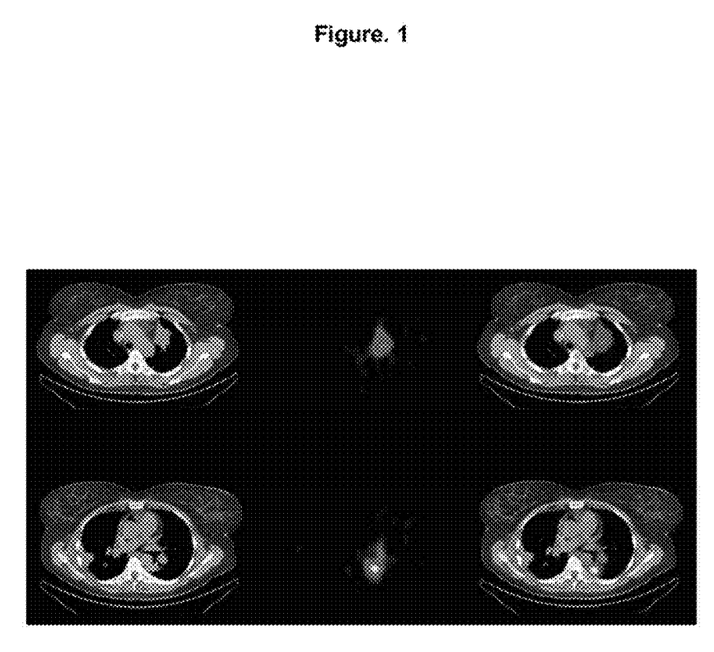
FIG. 1—Plain CT (upper rows) and Bremsstrahlung-SPECT (lower rows) after Y90 radioembolization of segments 1-3 and 6 of the left lung in patient 1 with mCRC. The dose uptake is visually limited to the metastases FIG. 2—Baseline (upper row) and CT at 6 weeks postradioembolization (lower row) (patient 1). Two target lesions (straight arrows) either stable or in remission, whereas an untreated lesion on the right is massively progressive (curved arrow). This lesion underwent percutaneous irradiation afterwards FIG. 3—Selective injection into a bronchial artery feeding numerous metastases of renal cell cancer (patient 2)

Dosimetry for Y90-radioembolization assumed a conservative scenario of homogenous dose distribution in the targeted lung, i.e., tumor uptake ratio of 1:1. Following the recommendations of Ho et al. [Ho 5, Lau W Y, Leung T W, Chan M, Johnson P J, Li A K (1997) Clinical evaluation of the partition model for estimating radiation doses from yttrium-90 microspheres in the treatment of hepatic cancer. Clin Nucl Med 24(3):293-298], the maximum dose exposure was limited to one lung to 30 Gy. A CT-based volumetry served to determine the according dose. We injected 200 MBq Y90-resin microspheres (Sirtex Inc., Australia) in the feeding bronchial artery of the targeted segments. In contrast to our conservative dosimetric assumptions of a tumor uptake ratio of 1:1, Y90-PET and Bremsstrahlung-SPECT revealed a dose uptake visually limited to the metastases (FIG. 1). Pronounced Y90 activity was detected in neither lung parenchyma nor the chest wall.

Figure 2:
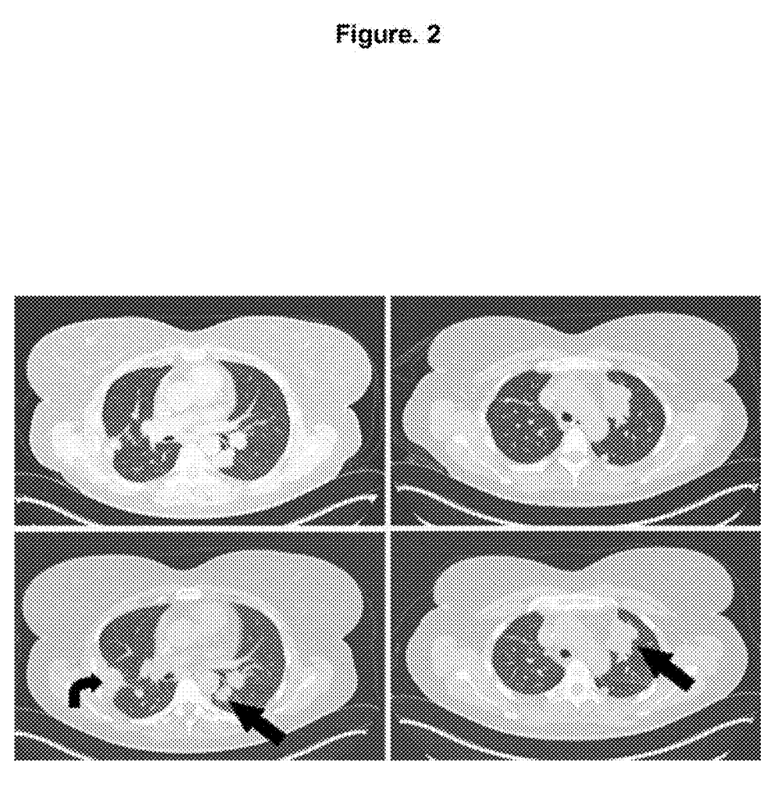

Physical examination and lung function tests remained unchanged and within normal limits at 4 weeks follow-up. CT between 4 and 12 weeks revealed no signs of lung pneumonitis. Lung nodules targeted by the radioembolization showed stable disease or partial remission according to RECIST 1.1 criteria, whereas non-target nodules in the contralateral lung showed progressive disease (FIG. 2). The patient received local ablations of the remaining tumors and she was alive, however, progressive with new metastases, 9 months after her initial presentation.

Patient 2

Figure 3:
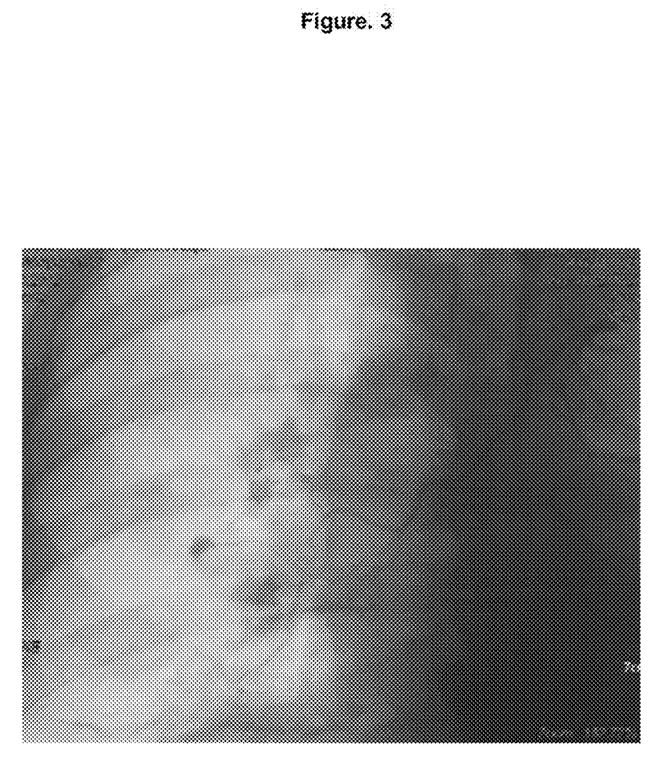
Figure 4:
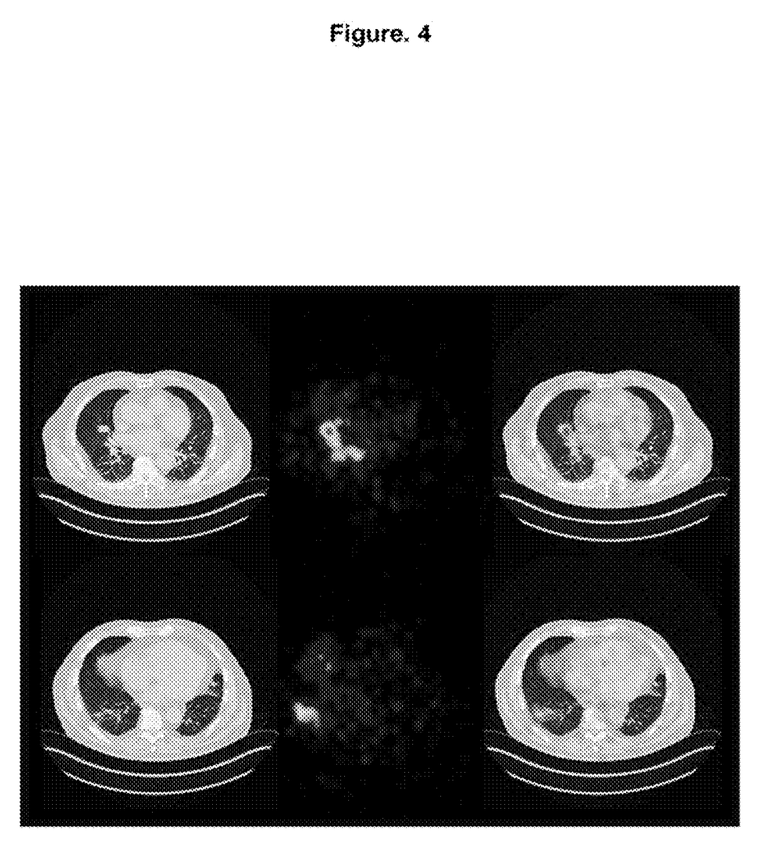
FIG. 4—Y90-PET post radioembolization showing tumor uptake and no visual accumulation in normal parenchyma or chest wall (patient 2)

The second patient was a 69-year-old male with a history of renal cell carcinoma diagnosed in 2006 with subsequent lung metastases in 2008. He had undergone systemic treatments with sunitinib and was switched to Nexavar upon tumor progression. Due to severe side effects, including hand-foot syndrome, fatigue, and diarrhoea, the dose was lowered to 100 mg bid and ultimately discontinued. A brain metastasis was resected surgically. After local ablations of lung metastases in 2009 and 2011, the patient presented with diffuse lung metastases in both upper lungs not amenable to further local ablation or surgery. The patient refused a systemic third line agent due to his history of toxicities from targeted agents. The inter-disciplinary decision was to offer cytoreduction as indicated by the ESMO guidelines specifically for renal cell cancer with lung only disease by a combination of a locoregional lung RE and further local ablation if necessary. The patient was evaluated for Y90-radioembolization of the lung. Respiratory function tests were normal, and angiography revealed strongly hyperperfused lung metastases (FIG. 3). Angiographic workup and the assumptions for dosimetry were equal to patient 1. We injected 80 MBq Tc99m-MAA via a microcatheter in the right bronchial artery feeding segments 4-6 as well as a minor proportion of the mediastinum. One week later, Y90 radioembolization was performed by injecting 195 MBq in the feeding bronchial artery (FIG. 4).

Lung function tests and CT 4 weeks later revealed no functional impairment or signs of lung pneumonitis. We thus evaluated the left upper lung lobe segments 1-3 with 80 MBq Tc99m-MAA followed by Y90-radioembolization with 180 MBq a week later. Clinical examinations as well as CT follow-up after 4 weeks did not show any signs of functional or morphological impairment in both lungs. Lesions exposed to Y90 remained stable or displayed partial remission according to RECIST 1.1, whereas lesions missed by radioembolization were slowly progressive. Before further local ablations were scheduled as initially intended the patient died of unknown causes 6 months after radioembolization.

Summary of Results

The concept of delivering Y90-labeled microspheres to lung malignancies is specifically interesting for patients who have failed systemic chemotherapy. In our patients, no adverse events were noted from radiation exposure to the lungs. Despite application of the dose in bronchial arteries supplying several segments, no signs of radiation pneumonitis were detected in follow-up CT, and there were no clinical changes in the lung function parameters of either patient. It is noteworthy that visually the degree of Y90 accumulation in the metastatic lung lesions was extraordinary high compared with the pattern commonly experienced during radioembolization of liver tumors. Kennedy et al. [Kennedy A S, Nutting C, Coldwell D, Gaiser J, Drachenberg C (2004) Pathologic response and microdosimetry of (90)Y microspheres in man: review of four explanted whole livers. Int J Radiat Oncol Biol Phys 60(5)1 552-1563] reported a tumor uptake ratio in mCRC of the liver of 2.1-2.5, whereas in both the patients studied both SPECT and Y90-PET demonstrated uptake in the targeted tumors only. From this the inventors hypothesize that the blood pool of bronchial arteries, including their capillary system, is low compared with normal arterial liver supply. Hence, embolization with resin microspheres may have induced an early temporary occlusion of bronchial artery supply to normal bronchi, with consecutive enhanced accumulation of the substrate in the lung lesions irrespective of high or low perfusion characteristic in the respective lesions of either renal or colorectal origin. Such an effect was visible in both patients via fluoroscopy during radioembolization.

The dose delivered in our patients was 200 MBq per treatment, which is low compared with radioembolization of the liver. We base the following assumptions on equations established by MIRD that 1 GBq (27 mCi) of Y90 delivers a total dose of 50 Gy/kg in tissue [Kennedy A S, Dezarn W A, McNeillie P, Coldwell D, Nutting C, Carter D et al (2008) Radioembolization for unresectable neuroendocrine hepatic metastases using resin 90Y-microspheres: early results in 148 patients. Am J Clin Oncol 31(3): 271-279]. The comparatively low doses sufficed to achieve response in our patients, because the tumor uptake ratio in lung was much different from that experienced in liver. As can be seen on the SPECT and Y90-PET images (FIGS. 1 and 4), our patients had an almost exclusive uptake in the lung lesions. In patient 1, the calculation for the effective tumor dose with a tumor volume of 40 ml was as follows: the injection of 200 MBq (equals 5.6 mCi) resulted in a tumor dose of up to 5 MBq/ml (equals 250 Gy) if the dose to the bronchial arterial system is considered negligible as indicated by SPECT or Y90-PET.

The variable anatomy of the bronchial artery supply to the lungs is an obstacle of the technique described, which will make standardization of the technique in future clinical studies difficult. In addition to the thoracic aorta, bronchial supply may derive from intercostal arteries, subclavian arteries, the internal thoracic artery, inferior phrenic artery, etc. In this situation, CT angiography (CTA) before the intervention might improve therapy planning. The observations described in this article have been made in two subjects only, and the value of our assumptions remains unclear. As a consequence, we are tentatively planning a Phase I trial to assess safety and derive preliminary efficacy data for Y90 radioembolization of lung malignancies via the bronchial artery.

In conclusion, access to primary or secondary malignancies via the bronchial artery is feasible. The deposition of radioactive particles such as Y90-resin-microspheres sufficient to achieve a reasonable absorbed dose in the tumors was technically feasible in two patients. However, open questions remain regarding dosimetry and safe dose exposure to the lung. The technique warrants thorough investigation before clinical use.

The invention claimed is:

1. A method for treating a lung neoplasia in a subject in need of treatment comprising subjecting the subject to selective internal radiation therapy with irradiated microparticles, wherein (i) the irradiated microparticles have a prescribed activity of 150 to 300 MBq and (ii) the therapy delivers a tumor dose of up to 6 MBq/ml of tumor volume to a site of treatment in the lung.

2. A method according to claim 1 wherein the site of treatment is restricted to the neoplasia.

3. A method according to claim 1 wherein the activity of the irradiated microparticles used in the selective internal radiation therapy is 180 to 250 MBq.

4. A method according to claim 1 wherein the activity of the irradiated microparticles used in the selective internal radiation therapy is approximately 200 MBq.

5. A method according to claim 1 wherein the therapy delivers a tumor dose of up to 5 MBq/ml of tumor volume to the site of treatment in the lung.

6. A method according to claim 1 wherein the therapy delivers a tumor dose of between 4 and 5 MBq/ml of tumor volume to the site of treatment in the lung.

7. A method according to claim 1 wherein the therapy is combined with a chemotherapeutic agent suitable for lung neoplastic treatment.

* * * * *